United States Patent [19]

Slaugh

[11] Patent Number: 4,571,445

[45] Date of Patent: Feb. 18, 1986

[54] PROCESS FOR REMOVAL OF SULFUR COMPOUNDS FROM CONJUGATED DIOLEFINS

[75] Inventor: Lynn H. Slaugh, Cypress, Tex.

[73] Assignee: Shell Oil Company, Houston, Tex.

[21] Appl. No.: 685,653

[22] Filed: Dec. 24, 1984

[51] Int. Cl.$^4$ ................................................. C07C 7/00
[52] U.S. Cl. .................................... 585/852; 585/853; 208/230; 208/213; 208/226; 502/415
[58] Field of Search ................ 585/852, 853; 208/230, 208/213, 226; 502/415

[56] References Cited

U.S. PATENT DOCUMENTS

| | | | |
|---|---|---|---|
| 2,471,108 | 5/1949 | Hill | 208/230 |
| 2,748,059 | 5/1956 | Nixon et al. | 208/230 |
| 2,845,382 | 7/1958 | Leum | 208/226 |
| 2,877,176 | 3/1959 | Wolff et al. | 208/230 |
| 3,496,098 | 2/1970 | Rothe | 208/230 |
| 3,694,350 | 9/1972 | Wennerberg | 208/213 |
| 3,761,534 | 9/1973 | Sun et al. | 208/230 |
| 3,920,540 | 11/1975 | McCoy et al. | 208/213 |
| 4,003,823 | 1/1977 | Baird, Jr. et al. | 208/230 |
| 4,007,109 | 2/1977 | Baird, Jr. et al. | 208/230 |
| 4,127,470 | 11/1978 | Baird, Jr. et al. | 208/213 |
| 4,433,981 | 2/1984 | Slaugh et al. | 55/59 |

Primary Examiner—John Doll
Assistant Examiner—Helane Myers
Attorney, Agent, or Firm—Ronald R. Reper

[57] ABSTRACT

A process is disclosed for reducing the level of sulfur compounds from liquid conjugated diolefin hydrocarbons by contacting said sulfur compound-bearing hydrocarbon liquids with sorbents prepared by combining particulate alumina with at least one compound decomposable to of sodium oxide, barium oxide, calcium oxide or a salt decomposable to potassium oxide, but excluding potassium carbonate and potassium bicarbonate and calcining. The process is particularly useful for removal of hydrogen sulfide and carbon disulfide from butadiene and isoprene.

10 Claims, No Drawings

PROCESS FOR REMOVAL OF SULFUR COMPOUNDS FROM CONJUGATED DIOLEFINS

FIELD OF INVENTION

This invention relates to a process for removing materials which inhibit polymerization of polymerizable conjugated diolefin hydrocarbons. The process is particularly useful for removing sulfur compounds such as carbon disulfide from butadiene and isoprene.

BACKGROUND OF THE INVENTION

Conventionally, after their manufacture, conjugated diolefins such as aliphatic diolefins often contain minor amounts e.g., 5–200 ppm of sulfur compounds, such as hydrogen sulfide and particularly carbon disulfide, either added as an inhibitor or as an impurity arising from the manufacturing process. Removal of these materials is important in many processes employing the conjugated diolefin(s) as feed material, particularly in the production of high molecular weight polymers useful as elastomers, plastics, thermoplastic elastomers and the like.

When e.g., hydrogen sulfide or carbon disulfide is present in the monomeric conjugated diolefin, it often acts as an inactivator or poison for the initiator employed in the polymerization process. Accordingly, many processes apply an excess of costly initiator to compensate for the sulfur compounds e.g., carbon disulfide present. Unfortunately, the reaction products of the carbon disulfide and initiator remain in the polymer product and can cause odor problem as well as sometimes interfering with subsequent chemical processing of the polymer, such as e.g., selective hydrogenation.

The present invention provides a method for removing carbon disulfide from liquid conjugated diolefin streams by contacting with certain sorbents. The use of very similar sorbents to remove carbon dioxide from gaseous streams in disclosed in U.S. Pat. No. 4,433,981 issued to L. H. Slaugh and C. L. Willis. However, some of the sorbents disclosed in said patent have been found too active for use with conjugated diolefins resulting in polymerization and/or gelation in the particulate sorbent bed within a short time after contact with the conjugated diolefin.

SUMMARY OF THE INVENTION

This invention provides a method for reducing the level of sulfur compounds selected from hydrogen sulfide and carbon disulfide in a sulfur compound-containing liquid conjugated diolefin which comprises contacting said liquid olefin at a temperature up to about the boiling point of said liquid with an sorbent prepared by combining a porous particulate alumina with a compound decomposable to sodium oxide, barium oxide, calcium oxide or a compound decomposable to potassium oxide excluding potassium carbonate or bicarbonate, and calcining the resultant alumina product. The sorbent materials can be readily regenerated e.g., by heating alone or being swept by hot inert gas. The sorbent is a solid, stable, relatively non-toxic inexpensive material that can be readily used in packed beds with little or no dusting or carryover of fines. Preferred sorbents are KOH-alumina, NaOH-alumina and $Na_2CO_3$—$Al_2O_3$.

DESCRIPTION OF THE PREFERRED EMBODIMENTS

The conjugated diolefins to be treated according to the inhibitor removal process of the invention will generally have an atmospheric boiling point in the range from about $-5°$ C. to about $45°$ C. and will include butadiene; isoprene; cis-piperylene; and trans-piperylene.

The contacting of the conjugated diolefin with the sorbent according to the invention may take place in any known solids-liquid contacting process e.g., by slurrying with subsequent filtration to separate the solid sorbent, however, preferably, and most conveniently, the inhibitors are removed by passing the conjugated diolefin liquid through a bed of the granular sorbent at space velocities of 0.01 to about 50 and preferably about 2 to about 20. The contact bed may be in any configuration adapted for the desired flow rate and sulfur compound content of the conjugated diolefin.

The alumina sorbents of this invention are prepared, for example, by impregnating or providing an alumina with alkali metal or alkaline earth metal compounds decomposable to the oxide during calcination by forming a composition of alumina and an alkali metal oxide and/or an alkaline earth metal oxide, and then calcining the resultant composition. It is thought that in most cases the alkali metal and alkaline earth metal compounds during calcination react after intermediate oxide formation with the alumina to form a metal aluminate. Suitable impregnating alkali or alkaline earth metal compounds are their hydroxides, cyanides, cyanates, chelates, alkoxylates and salts of other weak acids such the acetates or salts of strong acids that decompose upon calcination such as the nitrates. Carbonates and bicarbonates of e.g., sodium, barium and calcium may be used, however, the carbonates and bicarbonate of potassium may not, as the latter two compounds result in unsuitable sorbents which interact with the diolefin. Calcination temperatures range from about $350°$ C. to about $600°$ C., preferably from about $350°$ C. to about $550°$ C. The calcination is carried out in any atmosphere: vacuum, reducing, neutral or oxidizing. It is preferred to carry out the calcining in a dry neutral atmosphere such as nitrogen or argon, or an oxidizing atmosphere such as air or oxygen. Air is preferred. Oxygen, in many cases, can contaminate feed stocks, so that when an oxygen-containing gas is used for calcining, it is frequently advantageous to do the latter stages of calcination in neutral or reducing atmosphere in order to sweep out any oxygen from the sorbent. Calcining times are not critical and depend on calcining temperature, higher temperatures requiring shorter times. Typical times range from about 0.1 to about 50 hours. The time-temperature combination selected should be such that the alkali metal or alkaline earth metal compound substantially reacts with the alumina.

For regeneration, if heat alone is used the sorbents are regenerated by reheating to calcining conditions, i.e., to about $350°$ C.–$550°$ C., in any atmosphere, reducing, neutral or oxidizing. For regeneration using a non-carbon disulfide containing gas to sweep through the sorbent lower temperatures e.g., from $200°$–$500°$ C. are suitable. When carbonaceous materials such as tar or coke are present on the sorbent, the regeneration is preferably carried out in an oxygen-containing atmosphere, such as air, while preferably controlling the amount of oxygen to prevent temperatures in substantial excess of about 600° C. Excess temperatures cause sintering and loss of surface area. As in calcining, it may be desirable to purge material regenerated in an oxygen-containing atmosphere with a neutral or reducing gas.

The alkali metals used to form the catalyst of this invention are potassium and sodium, while the alkaline earth metals include calcium, and barium. Combinations of alkali metals and/or alkaline earth metals can be used. Preferred impregnating materials for the alumina are sodium carbonate and bicarbonate, and potassium hydroxide. For isoprene streams potassium hydroxide is preferred. The sorbent capacity is determined by the amount of basic sites formed upon calcination.

The alumina employed can be any of the variety of available aluminas or alumina hydrates, such as alumina gel, activated alumina, gamma alumina, etc. Regarding purity of the alumina, it may be stated that small amounts of impurities are not generally detrimental. The most suitable aluminas for use in the present invention are found to be those having a high surface area, for instance, alumina having a surface area of at least about 100 $M^2/g$ and preferably at least about 200 $M^2/g$. The alumina may contain minor amounts of other compounds such as silica. Aluminas are readily available commercially which are readily usable in the instant invention. The following Table I lists several commercial aluminas and their properites which are found suitable.

TABLE I

| Alumina | Surface Area, $m^2$g | Pore Vol., Co/gm | Na, ppm | $SO_4^=$, % wt | $Fe_2O_3$, % wt | Cl, % wt |
|---|---|---|---|---|---|---|
| CCI[a] | 252 | 0.8 | 160 | 0.06 | — | 0.02 |
| KA-201[b] | 365 | 0.42 | 600 | 0.03 | — | 0.01 |
| RA-1[c] | 263 | 0.26 | 4700 | 0.02 | 0.18 | — |
| ACCO[d] | 225 | 0.68 | 580 | 0.6 | — | 0.6 |
| Norton | 218 | 0.62 | 0.51 | 0.03 | — | 0.03 |
| CATAPAL[e] | 348 | 0.91 | — | — | — | — |
| FILTROL[f] | 214 | 0.82 | — | — | — | — |
| Alcoa F-1 | 210 | 0.51 | — | — | — | — |

[a]Catalysts & Chemicals, Inc., now United Catalysts
[b]Kaiser
[c]Reynolds Corporation
[d]American Cyanamid Corporation
[e]Conoco Corporation
[f]Filtrol Corporation Known methods for adding the component(s) e.g., sodium carbonate or sodium bicarbonate to the alumina can be employed. A preferred method is to soak the alumina pellets or particles in an aqueous solution of the desired compound, e.g., an alkali or alkaline earth metal hydroxide, and then convert the impregnated compound to the corresponding alkali or alkaline earth metal basic sites by drying and calcining at temperatures from about 350° C. to about 600° C. Dry impregnation can be suitably used. Since the impregnating compound is primarily reacting with the surface of the alumina, both external and internal pore surface, then the maximum amount of impregnating compound that can be effectively utilized will depend on the surface area. Of course, lesser amounts can be used. Ordinarily, the molar ratio of alkali metal to alumina will range from about 1:1 to about 1:50, preferably from about 1:1 to about 1:25 and the ratio of alkaline earth metal to alumina will range from about 1:1 to about 1:100 preferably from about 1:2 to about 1:50.

The sorbent is effective up to temperatures the boiling point of the liquid conjugation diolefin. There is no particular lower limit on the temperature. The lower limit is determined by the particular hydrocarbon stream being processed and the temperature at which it solidifies or becomes too viscous to process.

The sorbent is used in typical fashion. It is preferably used in a packed bed or column. The use of dual columns allow one to be regenerated for sorbing additional carbon disulfide while the other is sorbing.

The process of this invention is illustrated by the following examples which are provided for illustration and comparative purposes and are not to be construed as limiting the invention.

EXAMPLE I

The following example typifies the production of sorbents used in the invention.

7 Grams of C.P. grade sodium carbonate is dissolved in 26 mls of deionized water. This solution is poured on 40 gms of Kaiser grade KA-201 alumina (20–30 mesh) while the latter is being stirred. The volume of solution and the weight of alumina is proportioned essentially to fill the pores in the alumina without excess solution (dry impregnation). The impregnated material is dried at 100° C. in air. The composition is then calcined in air for 16 hours at 500° C., resulting that the composition contains about 7 percent by weight of sodium measured as the metal.

Similar sorbents are prepared, for example by using solutions of sodium bicarbonate, potassium hydroxide, calcium nitrate, and barium acetate.

EXAMPLE II

The following example illustrates the use of various sorbents according to the invention for adsorbing carbon disulfide from a liquid isoprene stream.

Several catalysts are prepared according to the teaching of Example I by impregnating Kaiser KA 201 alumina (⅛" spheres) with solutions of the compounds of sodium, potassium and barium listed in Table II, drying and calcining in air at a temperature of about 500° C. A reactor having dimensions of about 1 inch diameter×9 inch length was loaded with each said sorbent and passivated by flowing about one bed volume of dry cyclohexane therethrough at room temperature and atmospheric pressure. A commercial polymerization grade isoprene, after passing through a guard bed of alumina to remove any moisture and tert-butyl catechol present was injected with carbon disulfide to a total carbon disulfide content of 40 ppm and passed through the sorbtion beds at the conditions shown in Table II. After contacting each sorbent for the equivalent bed weight shown in Table II, a sample of liquid is withdrawn and analyzed for carbon disulfide content. From the reduction in carbon disulfide content, the amount of carbon disulfide extraction is determined. Results using potassium carbonate, sodium carbonate, barium acetate and potassium hydroxide are listed in Table II.

TABLE II

| | SORBENT PERFORMANCE SUMMARY | | | |
|---|---|---|---|---|
| Sorbent Type | Treated Feed, Equiv. Bed Wts, | Rate S.L.V. ft/min. | W.H.S.V. gms/gm/hr | Extraction, % w $CS_2$ |
| Potassium Carbonate on KA-201 Alumina | 1 | 0.10 | 7.9 | (1) |
| Sodium Carbonate on KA-201 | 12 | 0.016 | 1.0 | — |
| | 39 | 0.016 | 1.0 | 100 |
| | 51 | 0.016 | 1.0 | 100 |

TABLE II-continued

SORBENT PERFORMANCE SUMMARY

| Sorbent Type | Treated Feed, Equiv. Bed Wts, | Rate S.L.V. ft/min. | W.H.S.V. gms/gm/hr | Extraction, % w $CS_2$ |
|---|---|---|---|---|
| Alumina | 75 | 0.016 | 1.0 | 100 |
|  | 100 | 0.016 | 1.0 | 100 |
|  | 115 | 0.016 | 1.0 | 86 |
| Barium | 10 | 0.023 | 1.37 | 100 |
| Acetate | 43 | 0.023 | 1.37 | 100 |
| on KA-201 | 77 | 0.023 | 1.37 | 56 |
|  | 107 | 0.023 | 1.37 | 50 |
| Potassium | 22 | 0.025 | 1.56 | 100 |
| Hydroxide | 57 | 0.025 | 1.56 | 100 |
| on KA-119 | 119 | 0.025 | 1.56 | 100 |
| Alumina | 168 | 0.025 | 1.56 | 100 |

(1)No analysis due to polymerization of feed in column.

These data show that use of potassium carbonate results in a rapid polymerization and gelation of the isoprene feed, and is thereby unsuitable. The other compounds are all successful in removing 100% of the carbon disulfide up to 43 sorbent bed weights of feed treatment; and remains at 100% up to 100 bed weights of sodium carbonate and at 100% up to 168 bed weights for potassium hydroxide when the test was discontinued for that sorbent.

What is claimed is:

1. A process for reducing the level of sulfur compounds selected from hydrogen sulfide and carbon disulfide in a sulfur compound-containing liquid conjugated diolefin hydrocarbon having an atmospheric boiling point in the range from about −5° to about 45° C. which comprises contacting said liquid diolefin at a temperature up to about the boiling point of said liquid diolefin with a sorbent prepared by combining a porous particulate alumina having a surface area of about 100 to 365, $M^2$ per gram with a compound decomposable to sodium oxide, barium oxide, calcium oxide or a compound decomposable to potassium oxide, but excluding the carbonate or bicarbonate of potassium; and calcining the resultant alumina product at a temperature from about 350° to about 600° C.

2. The process of claim 1, where in the sorbent the molar ratio of sodium or potassium metal to alumina ranges from about 1:1 to about 1:50.

3. The process of claim 1, wherein the sorbent is prepared by impregnating with sodium carbonate, sodium bicarbonate or potassium hydroxide.

4. The process of claim 1, wherein the sorbent is prepared by impregnating alumina with a sodium or potassium salt.

5. The process of claim 1, where in preparation of the sorbent, the combined alumina is calcined at a temperature from about 350° to about 500° C.

6. The process of claim 1, wherein said liquid conjugated diolefin is selected from butadiene, isoprene and the piperylenes.

7. The process of claim 6, wherein said liquid olefin is isoprene.

8. The process of claim 1, where in the sorbent, the molar ratio of barium or calcium metal to alumina ranges from about 1:1 to about 1:100.

9. The process of claim 1, where in the sorbent is prepared by impregnating the alumina with a barium or calcium salt.

10. The process of claim 9, wherein the conjugated diolefin liquid is isoprene.

* * * * *